United States Patent
Zhang

(10) Patent No.: US 12,297,288 B2
(45) Date of Patent: May 13, 2025

(54) CD19-BASED CHIMERIC ANTIGEN RECEPTOR AND APPLICATION THEREOF

(71) Applicant: BEIJING MEIKANG GENO-IMMUNE BIOTECHNOLOGY CO., LTD., Beijing (CN)

(72) Inventor: Rui Zhang, Beijing (CN)

(73) Assignee: BEIJING MEIKANG GENO-IMMUNE BIOTECHNOLOGY CO., LTD., Beijing (CN)

(*) Notice: Subject to any disclaimer, the term of this patent is extended or adjusted under 35 U.S.C. 154(b) by 1301 days.

(21) Appl. No.: 16/971,971

(22) PCT Filed: Feb. 25, 2019

(86) PCT No.: PCT/CN2019/076050
§ 371 (c)(1),
(2) Date: Aug. 21, 2020

(87) PCT Pub. No.: WO2019/161796
PCT Pub. Date: Aug. 29, 2019

(65) Prior Publication Data
US 2020/0392248 A1    Dec. 17, 2020

(30) Foreign Application Priority Data
Feb. 23, 2018    (CN) .......................... 201810155428.1

(51) Int. Cl.
*C07K 16/30*    (2006.01)
*A61K 35/17*    (2015.01)
(Continued)

(52) U.S. Cl.
CPC ...... *C07K 16/3061* (2013.01); *A61K 39/4611* (2023.05); *A61K 39/4631* (2023.05);
(Continued)

(58) Field of Classification Search
CPC ............. C07K 16/3061; A61P 35/02; A61K 39/001112; A61K 35/17
See application file for complete search history.

(56) References Cited

U.S. PATENT DOCUMENTS

| | | | |
|---|---|---|---|
| 10,266,592 B2 | 4/2019 | Jensen | |
| 2004/0002158 A1* | 1/2004 | Chang | C12N 15/86 435/235.1 |
| 2017/0137515 A1 | 5/2017 | Chang et al. | |

FOREIGN PATENT DOCUMENTS

| | | |
|---|---|---|
| CN | 106535925 A | 3/2017 |
| CN | 107245106 A | 10/2017 |

(Continued)

OTHER PUBLICATIONS

Grunder et al. Blood. 2012; 120(26):5153-5162. (Year: 2012).*
(Continued)

*Primary Examiner* — Taeyoon Kim
*Assistant Examiner* — Jianjian Zhu
(74) *Attorney, Agent, or Firm* — Wood, Phillips, Katz, Clark & Mortimer

(57) ABSTRACT

The present application provides a chimeric antigen receptor and application thereof. The chimeric antigen receptor comprises an antigen-binding domain, a transmembrane domain, a costimulatory signal transduction region, a CD3ζ signal transduction domain, and an inducible suicide fusion domain in tandem arrangement; wherein the antigen-binding domain binds to a tumor surface antigen and the tumor surface antigen is CD19.

9 Claims, 6 Drawing Sheets
Specification includes a Sequence Listing.

(51) Int. Cl.
  *A61K 39/00* (2006.01)
  *A61P 35/02* (2006.01)
  *C07K 14/705* (2006.01)
  *C07K 14/725* (2006.01)
  *C07K 16/10* (2006.01)
  *C12N 5/0783* (2010.01)

(52) U.S. Cl.
  CPC ...... *A61K 39/464412* (2023.05); *A61P 35/02* (2018.01); *C07K 14/7051* (2013.01); *C07K 14/70521* (2013.01); *C07K 14/70578* (2013.01); *C07K 16/1045* (2013.01); *C12N 5/0636* (2013.01); *A61K 2039/804* (2018.08); *A61K 2239/38* (2023.05); *A61K 2239/48* (2023.05)

(56) References Cited

FOREIGN PATENT DOCUMENTS

| | | | | |
|---|---|---|---|---|
| CN | 107245107 A | 10/2017 | | |
| CN | 107312091 A | 11/2017 | | |
| CN | 107312097 A | 11/2017 | | |
| CN | 107312098 A | 11/2017 | | |
| CN | 107337737 A | 11/2017 | | |
| CN | 107400168 A | * 11/2017 | ............. | A61K 35/17 |
| CN | 108383914 A | 8/2018 | | |
| JP | 2017518037 A | 7/2017 | | |
| WO | WO-2017024318 A1 | * 2/2017 | ......... | A61K 31/4525 |
| WO | 2017181110 A1 | 10/2017 | | |

OTHER PUBLICATIONS

Xu et al., Human Vaccines & Immunotherapeutics. 2017; 13(7): 1548-1555. (Year: 2017).*
Office Action for corresponding Japanese Application No. 2020-568017.
Office Action for corresponding Chinese Application No. 201801554281.
Sadelain, "CAR Therapy: the CD19 paradigm", J Clin Invest. 2015;125(9):3392-3400. https://doi.org/10.1172/JCI80010.cl.
International Search Report for corresponding PCT Application No. PCT/CN2019/076050 mailed May 21, 2019.

* cited by examiner

SEQUENCE LISTING

```
<160> NUMBER OF SEQ ID NOS: 11

<210> SEQ ID NO 1
<211> LENGTH: 245
<212> TYPE: PRT
<213> ORGANISM: Artificial Sequence
<220> FEATURE:
<223> OTHER INFORMATION: tumor surface antigen CD19

<400> SEQUENCE: 1

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110

Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
```

```
                195                 200                 205
Ser Leu Gln Thr Asp Thr Ala Ile Tyr Tyr Cys Ala Lys His Tyr
    210                 215                 220
Tyr Tyr Gly Gly Ser Tyr Ala Met Asp Tyr Trp Gly Gln Gly Thr Ser
225                 230                 235                 240
Val Thr Val Ser Ser
                245

<210> SEQ ID NO 2
<211> LENGTH: 48
<212> TYPE: PRT
<213> ORGANISM: Artificial Sequence
<220> FEATURE:
<223> OTHER INFORMATION: CD27 signal transduction domain

<400> SEQUENCE: 2

Gln Arg Arg Lys Tyr Arg Ser Asn Lys Gly Glu Ser Pro Val Glu Pro
1               5                   10                  15
Ala Glu Pro Cys His Tyr Ser Cys Pro Arg Glu Glu Glu Gly Ser Thr
                20                  25                  30
Ile Pro Ile Gln Glu Asp Tyr Arg Lys Pro Glu Pro Ala Cys Ser Pro
            35                  40                  45

<210> SEQ ID NO 3
<211> LENGTH: 423
<212> TYPE: PRT
<213> ORGANISM: Artificial Sequence
<220> FEATURE:
<223> OTHER INFORMATION: inducible suicide fusion domain iCasp9

<400> SEQUENCE: 3

Gly Ser Gly Ala Thr Asn Phe Ser Leu Leu Lys Gln Ala Gly Asp Val
1               5                   10                  15
Glu Glu Asn Pro Gly Pro Met Gly Val Gln Val Glu Thr Ile Ser Pro
                20                  25                  30
Gly Asp Gly Arg Thr Phe Pro Lys Arg Gly Gln Thr Cys Val Val His
            35                  40                  45
Tyr Thr Gly Met Leu Glu Asp Gly Lys Lys Val Asp Ser Ser Arg Asp
    50                  55                  60
Arg Asn Lys Pro Phe Lys Phe Met Leu Gly Lys Gln Glu Val Ile Arg
65                  70                  75                  80
Gly Trp Glu Glu Gly Val Ala Gln Met Ser Val Gly Gln Arg Ala Lys
                85                  90                  95
Leu Thr Ile Ser Pro Asp Tyr Ala Tyr Gly Ala Thr Gly His Pro Gly
            100                 105                 110
Ile Ile Pro Pro His Ala Thr Leu Val Phe Asp Val Glu Leu Leu Lys
        115                 120                 125
Leu Glu Gly Gly Gly Ser Gly Gly Gly Ser Gly Ala Met Val
130                 135                 140
Gly Ala Leu Glu Ser Leu Arg Gly Asn Ala Asp Leu Ala Tyr Ile Leu
145                 150                 155                 160
Ser Met Glu Pro Cys Gly His Cys Leu Ile Ile Asn Asn Val Asn Phe
                165                 170                 175
Cys Arg Glu Ser Gly Leu Arg Thr Arg Thr Gly Ser Asn Ile Asp Cys
            180                 185                 190
Glu Lys Leu Arg Arg Arg Phe Ser Ser Leu His Phe Met Val Glu Val
        195                 200                 205
```

```
Lys Gly Asp Leu Thr Ala Lys Lys Met Val Leu Ala Leu Leu Glu Leu
    210                 215                 220

Ala Arg Gln Asp His Gly Ala Leu Asp Cys Cys Val Val Ile Leu
225                 230                 235                 240

Ser His Gly Cys Gln Ala Ser His Leu Gln Phe Pro Gly Ala Val Tyr
                    245                 250                 255

Gly Thr Asp Gly Cys Pro Val Ser Val Glu Lys Ile Val Asn Ile Phe
                260                 265                 270

Asn Gly Thr Ser Cys Pro Ser Leu Gly Gly Lys Pro Lys Leu Phe Phe
            275                 280                 285

Ile Gln Ala Cys Gly Gly Glu Gln Lys Asp His Gly Phe Glu Val Ala
    290                 295                 300

Ser Thr Ser Pro Glu Asp Glu Ser Pro Gly Ser Asn Pro Glu Pro Asp
305                 310                 315                 320

Ala Thr Pro Phe Gln Glu Gly Leu Arg Thr Phe Asp Gln Leu Asp Ala
                325                 330                 335

Ile Ser Ser Leu Pro Thr Pro Ser Asp Ile Phe Val Ser Tyr Ser Thr
                340                 345                 350

Phe Pro Gly Phe Val Ser Trp Arg Asp Pro Lys Ser Gly Ser Trp Tyr
            355                 360                 365

Val Glu Thr Leu Asp Asp Ile Phe Glu Gln Trp Ala His Ser Glu Asp
    370                 375                 380

Leu Gln Ser Leu Leu Arg Val Ala Asn Ala Val Ser Val Lys Gly
385                 390                 395                 400

Ile Tyr Lys Gln Met Pro Gly Cys Phe Asn Phe Leu Arg Lys Lys Leu
                405                 410                 415

Phe Phe Lys Thr Ser Ala Ser
                420

<210> SEQ ID NO 4
<211> LENGTH: 984
<212> TYPE: PRT
<213> ORGANISM: Artificial Sequence
<220> FEATURE:
<223> OTHER INFORMATION: Secretory-CD19-CD28-CD27-CD3?-2A-iCasp9

<400> SEQUENCE: 4

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
                20                  25                  30

Leu Ser Ala Ser Leu Gly Asp Arg Val Thr Ile Ser Cys Arg Ala Ser
            35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
                100                 105                 110

Gly Asn Thr Leu Pro Tyr Thr Phe Gly Gly Gly Thr Lys Leu Glu Ile
            115                 120                 125

Thr Gly Ser Thr Ser Gly Ser Gly Lys Pro Gly Ser Gly Glu Gly Ser
    130                 135                 140
```

```
Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
            165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
            195                 200                 205

Ala Leu Lys Ser Arg Leu Thr Ile Ile Lys Asp Asn Ser Lys Ser Gln
            210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Gly Gly Ser Tyr Ala Met Asp Tyr
                245                 250                 255

Trp Gly Gln Gly Thr Ser Val Thr Val Ser Ser Ala Ala Ile Glu
            260                 265                 270

Val Met Tyr Pro Pro Pro Tyr Leu Asp Asn Glu Lys Ser Asn Gly Thr
            275                 280                 285

Ile Ile His Val Lys Gly Lys His Leu Cys Pro Ser Pro Leu Phe Pro
    290                 295                 300

Gly Pro Ser Lys Pro Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335

Arg Ser Lys Arg Ser Arg Leu Leu His Ser Asp Tyr Met Asn Met Thr
            340                 345                 350

Pro Arg Arg Pro Gly Pro Thr Arg Lys His Tyr Gln Pro Tyr Ala Pro
            355                 360                 365

Pro Arg Asp Phe Ala Ala Tyr Arg Ser Ala Ser Gly Gly Gly Gly Ser
            370                 375                 380

Gly Gly Gly Gly Ser Gln Arg Arg Lys Tyr Arg Ser Asn Lys Gly Glu
385                 390                 395                 400

Ser Pro Val Glu Pro Ala Glu Pro Cys His Tyr Ser Cys Pro Arg Glu
                405                 410                 415

Glu Glu Gly Ser Thr Ile Pro Ile Gln Glu Asp Tyr Arg Lys Pro Glu
            420                 425                 430

Pro Ala Cys Ser Pro Gly Gly Gly Ser Gly Gly Gly Gly Ser Arg
            435                 440                 445

Val Lys Phe Ser Arg Ser Ala Asp Ala Pro Ala Tyr Gln Gln Gly Gln
450                 455                 460

Asn Gln Leu Tyr Asn Glu Leu Asn Leu Gly Arg Arg Glu Glu Tyr Asp
465                 470                 475                 480

Val Leu Asp Lys Arg Arg Gly Arg Asp Pro Glu Met Gly Gly Lys Pro
            485                 490                 495

Arg Arg Lys Asn Pro Gln Glu Gly Leu Tyr Asn Glu Leu Gln Lys Asp
            500                 505                 510

Lys Met Ala Glu Ala Tyr Ser Glu Ile Gly Met Lys Gly Glu Arg Arg
            515                 520                 525

Arg Gly Lys Gly His Asp Gly Leu Tyr Gln Gly Leu Ser Thr Ala Thr
            530                 535                 540

Lys Asp Thr Tyr Asp Ala Leu His Met Gln Ala Leu Pro Pro Arg Thr
545                 550                 555                 560

Ser Gly Ser Gly Ala Thr Asn Phe Ser Leu Leu Lys Gln Ala Gly Asp
```

```
              565                 570                 575
Val Glu Glu Asn Pro Gly Pro Met Gly Val Gln Val Glu Thr Ile Ser
            580                 585                 590

Pro Gly Asp Gly Arg Thr Phe Pro Lys Arg Gly Gln Thr Cys Val Val
            595                 600                 605

His Tyr Thr Gly Met Leu Glu Asp Gly Lys Lys Val Asp Ser Ser Arg
            610                 615                 620

Asp Arg Asn Lys Pro Phe Lys Phe Met Leu Gly Lys Gln Glu Val Ile
625                 630                 635                 640

Arg Gly Trp Glu Glu Gly Val Ala Gln Met Ser Val Gly Gln Arg Ala
                645                 650                 655

Lys Leu Thr Ile Ser Pro Asp Tyr Ala Tyr Gly Ala Thr Gly His Pro
                660                 665                 670

Gly Ile Ile Pro Pro His Ala Thr Leu Val Phe Asp Val Glu Leu Leu
                675                 680                 685

Lys Leu Glu Gly Gly Gly Ser Gly Gly Gly Ser Gly Ala Met
            690                 695                 700

Val Gly Ala Leu Glu Ser Leu Arg Gly Asn Ala Asp Leu Ala Tyr Ile
705                 710                 715                 720

Leu Ser Met Glu Pro Cys Gly His Cys Leu Ile Ile Asn Asn Val Asn
                725                 730                 735

Phe Cys Arg Glu Ser Gly Leu Arg Thr Arg Thr Gly Ser Asn Ile Asp
                740                 745                 750

Cys Glu Lys Leu Arg Arg Arg Phe Ser Ser Leu His Phe Met Val Glu
                755                 760                 765

Val Lys Gly Asp Leu Thr Ala Lys Lys Met Val Leu Ala Leu Leu Glu
                770                 775                 780

Leu Ala Arg Gln Asp His Gly Ala Leu Asp Cys Cys Val Val Val Ile
785                 790                 795                 800

Leu Ser His Gly Cys Gln Ala Ser His Leu Gln Phe Pro Gly Ala Val
                805                 810                 815

Tyr Gly Thr Asp Gly Cys Pro Val Ser Val Glu Lys Ile Val Asn Ile
                820                 825                 830

Phe Asn Gly Thr Ser Cys Pro Ser Leu Gly Gly Lys Pro Lys Leu Phe
                835                 840                 845

Phe Ile Gln Ala Cys Gly Gly Glu Gln Lys Asp His Gly Phe Glu Val
                850                 855                 860

Ala Ser Thr Ser Pro Glu Asp Glu Ser Pro Gly Ser Asn Pro Glu Pro
865                 870                 875                 880

Asp Ala Thr Pro Phe Gln Glu Gly Leu Arg Thr Phe Asp Gln Leu Asp
                885                 890                 895

Ala Ile Ser Ser Leu Pro Thr Pro Ser Asp Ile Phe Val Ser Tyr Ser
                900                 905                 910

Thr Phe Pro Gly Phe Val Ser Trp Arg Asp Pro Lys Ser Gly Ser Trp
                915                 920                 925

Tyr Val Glu Thr Leu Asp Asp Ile Phe Glu Gln Trp Ala His Ser Glu
                930                 935                 940

Asp Leu Gln Ser Leu Leu Leu Arg Val Ala Asn Ala Val Ser Val Lys
945                 950                 955                 960

Gly Ile Tyr Lys Gln Met Pro Gly Cys Phe Asn Phe Leu Arg Lys Lys
                965                 970                 975

Leu Phe Phe Lys Thr Ser Ala Ser
                980
```

<210> SEQ ID NO 5
<211> LENGTH: 2952
<212> TYPE: DNA
<213> ORGANISM: Artificial Sequence
<220> FEATURE:
<223> OTHER INFORMATION: Secretory-CD19-CD28-CD27-CD3?-2A-iCasp9

<400> SEQUENCE: 5

| | | | | | |
|---|---|---|---|---|---|
| atgctgctgc | tggtcacaag | cctgctgctg | tgcgagctgc | ccacccccgc | ctttctgctg | 60 |
| atccccgaca | tccagatgac | ccagaccacc | agcagcctga | gcgccagcct | gggcgacaga | 120 |
| gtgaccatca | gctgccgggc | cagccaggac | atcagcaagt | acctgaactg | gtatcagcag | 180 |
| aaacccgacg | gcaccgtgaa | gctgctgatc | taccacacca | gcggctgca | cagcggcgtg | 240 |
| cccagcagat | ttctggcag | cggatctggc | accgactaca | gcctgaccat | ctccaacctg | 300 |
| gaacaggaag | atatcgctac | ctacttctgt | cagcagggca | cacccctgcc | ctacaccttc | 360 |
| ggcggaggca | ccaagctgga | aatcaccggc | agcaccagcg | gctccggcaa | gcctggatct | 420 |
| ggcgagggca | gcaccaaggg | cgaagtgaag | ctgcaggaaa | gcggccctgg | cctggtcgcc | 480 |
| cctagccaga | gcctgtccgt | gacctgtacc | gtgtccggcg | tgtccctgcc | cgactacggc | 540 |
| gtgtcctgga | tcagacagcc | cccagaaag | ggcctggaat | ggctgggcgt | gatctggggc | 600 |
| agcgagacaa | cctactacaa | cagcgccctg | aagtcccggc | tgaccatcat | caaggacaac | 660 |
| agcaagagcc | aggtgttcct | gaagatgaac | agcctgcaga | ccgacgacac | cgccatctac | 720 |
| tactgcgcca | gcactacta | ctacggcggc | agctacgcca | tggactactg | gggccagggc | 780 |
| accagcgtga | cagtctcttc | tgcggccgca | attgaagtta | tgtatcctcc | tccttaccta | 840 |
| gacaatgaga | agagcaatgg | aaccattatc | catgtgaaag | ggaaacacct | ttgtccaagt | 900 |
| cccctatttc | ccggaccttc | taagcccttt | tgggtgctgg | tggtggttgg | gggagtcctg | 960 |
| gcttgctata | gcttgctagt | aacagtggcc | tttattattt | tctgggtgag | gagtaagagg | 1020 |
| agcaggctcc | tgcacagtga | ctacatgaac | atgactcccc | gccgcctgg | gcccacccgc | 1080 |
| aagcattacc | agccctatgc | cccaccacgc | gacttcgcag | cctatcgctc | cgctagcgga | 1140 |
| ggtggaggtt | ctggaggtgg | tggaagtcaa | agaaggaagt | accgcagcaa | caaaggagaa | 1200 |
| tctcccgtcg | agccagccga | gccctgtcat | tattcatgcc | caagggagga | ggagggaagt | 1260 |
| acaatcccaa | ttcaagaaga | ctacaggaag | cccgaacctg | catgcagtcc | aggtggaggc | 1320 |
| ggttctggag | gcggtggctc | ccgggtgaaa | ttctcacggt | ctgcagacgc | acccgcttac | 1380 |
| cagcaaggcc | agaaccaact | ctataacgag | ctcaatctag | gacgaagaga | ggagtacgat | 1440 |
| gttttggaca | agagacgtgg | ccgggaccct | gagatggggg | gaaagccgag | aaggaagaac | 1500 |
| cctcaggaag | gcctgtacaa | tgaactgcag | aaagataaga | tggcggaggc | ctacagtgag | 1560 |
| attgggatga | aggcgagcg | ccggaggggc | aaggggcacg | atggccttta | ccagggtctc | 1620 |
| agtacagcca | ccaaggacac | ctacgacgcc | cttcacatgc | aggccctgcc | cctcgcact | 1680 |
| agtggctccg | gagccacgaa | cttctctctg | ttaaagcaag | caggagacgt | ggaagaaaac | 1740 |
| cccggtccca | tggagtgca | ggtggaaacc | atctccccag | agacgggcg | caccttcccc | 1800 |
| aagcgcggcc | agacctgcgt | ggtgcactac | accgggatgc | ttgaagatgg | aaagaaagtg | 1860 |
| gactcctccc | gggacagaaa | caagccctt | aagtttatgc | taggcaagca | ggaggtgatc | 1920 |
| cgaggctgga | agaagggggt | tgcccagatg | agtgtgggtc | agagagccaa | actgactata | 1980 |
| tctccagatt | atgcctatgg | tgccactggg | cacccaggca | tcatcccacc | acatgccact | 2040 |

```
ctcgtcttcg atgtggagct tctaaaactg aaggtggag gcggttcagg cggcggcggc    2100
agcggcgcca tggtcggtgc tcttgagagt ttgaggggaa atgcagattt ggcttacatc    2160
ctgagcatgg agccctgtgg ccactgcctc attatcaaca atgtgaactt ctgccgtgag    2220
tccgggctcc gcacccgcac tggctccaac atcgactgtg agaagttgcg gcgtcgcttc    2280
tcctcgctgc atttcatggt ggaggtgaag ggcgacctga ctgccaagaa aatggtgctg    2340
gctttgctgg agctggcgcg gcaggaccac ggtgctctgg actgctgcgt ggtggtcatt    2400
ctctctcacg gctgtcaggc cagccacctg cagttcccag gggctgtcta cggcacagat    2460
ggatgccctg tgtcggtcga aagattgtg aacatcttca atgggaccag ctgccccagc     2520
ctgggaggga agcccaagct cttttcatc caggcctgtg tggggagca gaaagaccat      2580 gggtttgagg tggcctccac ttcccctgaa gacgagtccc ctggcagtaa ccccgagcca    2640
gatgccaccc cgttccagga aggtttgagg accttcgacc agctggacgc catatctagt    2700
ttgcccacac ccagtgacat ctttgtgtcc tactctactt tcccaggttt tgtttcctgg    2760
agggacccca agagtggctc ctggtacgtt gagaccctgg acgacatctt tgagcagtgg    2820
gctcactctg aagacctgca gtccctcctg cttagggtcg ctaatgctgt ttcggtgaaa    2880
gggatttata aacagatgcc tggttgcttt aatttcctcc ggaaaaaact tttctttaaa    2940
acatcagcta gt                                                        2952
```

<210> SEQ ID NO 6
<211> LENGTH: 39
<212> TYPE: PRT
<213> ORGANISM: Artificial Sequence
<220> FEATURE:
<223> OTHER INFORMATION: CD28 extracellular signal transduction domain

<400> SEQUENCE: 6

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro
        35

<210> SEQ ID NO 7
<211> LENGTH: 27
<212> TYPE: PRT
<213> ORGANISM: Artificial Sequence
<220> FEATURE:
<223> OTHER INFORMATION: CD28 transmembrane region conduction domain

<400> SEQUENCE: 7

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 8
<211> LENGTH: 43
<212> TYPE: PRT
<213> ORGANISM: Artificial Sequence
<220> FEATURE:
<223> OTHER INFORMATION: CD28 intracellular signal transduction domain

<400> SEQUENCE: 8

Arg Ser Lys Arg Ser Arg Leu Leu His Ser Asp Tyr Met Asn Met Thr
1               5                   10                  15

-continued

```
Pro Arg Arg Pro Gly Pro Thr Arg Lys His Tyr Gln Pro Tyr Ala Pro
                20                  25                  30

Pro Arg Asp Phe Ala Ala Tyr Arg Ser Ala Ser
        35                  40

<210> SEQ ID NO 9
<211> LENGTH: 22
<212> TYPE: PRT
<213> ORGANISM: Artificial Sequence
<220> FEATURE:
<223> OTHER INFORMATION: Secretory signal peptide

<400> SEQUENCE: 9

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 10
<211> LENGTH: 21
<212> TYPE: PRT
<213> ORGANISM: Artificial Sequence
<220> FEATURE:
<223> OTHER INFORMATION: Secretory signal peptide

<400> SEQUENCE: 10

Met Ala Leu Pro Val Thr Ala Leu Leu Leu Pro Leu Ala Leu Leu Leu
1               5                   10                  15

His Ala Ala Arg Pro
            20

<210> SEQ ID NO 11
<211> LENGTH: 22
<212> TYPE: PRT
<213> ORGANISM: Artificial Sequence
<220> FEATURE:
<223> OTHER INFORMATION: Secretory signal peptide

<400> SEQUENCE: 11

Met Leu Leu Leu Val Thr Ser Leu Leu Leu Cys Glu Leu Pro His Pro
1               5                   10                  15

Ala Phe Leu Leu Ile Pro
            20
```

CD19-BASED CHIMERIC ANTIGEN RECEPTOR AND APPLICATION THEREOF

TECHNICAL FIELD

The present application relates to the field of cellular immunotherapy for tumors, in particular to a CD19-based chimeric antigen receptor and application thereof, specifically to a method for constructing a chimeric antigen receptor T (CAR-T) cell technology based on the tumor specific target CD19 and its application in anti-tumor therapy.

BACKGROUND

B lymphocyte malignancies, including B cell acute lymphocytic leukemia (B-ALL), B cell lymphoma, and chronic lymphocytic leukemia (CLL), account for the majority of blood disease regardless of adults or children. Traditional methods for treating these patients include chemotherapy, radiotherapy, stem cell transplantation, small molecule drugs, and the use of antibody drugs. Although a part of patients can be cured by these therapies, many patients died due to the adverse reactions to the chemotherapy and radiotherapy, the tolerance to drugs, the ineffective transplantation, the refractory disease resulting from repeated recurrence and genetic mutations.

With the development of tumor immunology theory and clinical technology, the chimeric antigen receptor T-cell immunotherapy (CAR-T) has become one of the most promising tumor immunotherapies. The chimeric antigen receptor (CAR) typically consists of a tumor associated antigen-binding region, an extracellular hinge region, a transmembrane region, and an intracellular signal transduction region. Commonly, the CAR comprises a single chain fragment variable (scFv) region of an antibody or a binding domain specific for a tumor associated surface antigen (TAA), which is coupled to the cytoplasmic domain of a T cell signaling molecule via hinge and transmembrane regions. The most common lymphocyte activation moieties include a T cell costimulatory domain which is connected in tandem with a T cell effector function-triggering moiety (e.g. CD3ζ). The CAR-mediated adoptive immunotherapy allows CAR-transplanted T cells to directly recognize the TAAs on target tumor cells in a non-HLA-restricted manner. T cells are genetically modified to target antigens expressed on tumor cells through expression of CARs, and attempts in using genetically modified cells expressing CARs to treat these types of patients have achieved promising success.

CD19 molecule is a potential target for the treatment of hematological malignancies in B lymphocytes, and is also a focus in CAR research. The expression of CD19 is restricted to normal and malignant B cells and thus is a widely accepted CAR target for safety tests. Chimeric antigen receptor gene-modified T cells targeting CD19 molecules (CD19 CAR-T) have achieved great success in the treatment of multiple, refractory acute B lymphocytic leukemia.

CN 104788573 A discloses a chimeric antigen receptor hCD19scFv-CD8α-CD28-CD3ζ and use thereof. The chimeric antigen receptor is composed of variable regions of light and heavy chains of anti-human CD19 monoclonal antibody (hCD19scFv), a human CD8α hinge region, human CD28 transmembrane and intracellular regions, and a human CD3ζ intracellular region in tandem arrangement. However, the immune factor storm resulted from the CD19-based chimeric antigen receptor in the prior art has relatively strong toxicity and strong side effects.

Therefore, it is particularly important to find a chimeric antigen receptor with low side effects, good killing effect, and not easy to cause an immune factor storm.

SUMMARY OF THE INVENTION

The present application provides a CD19-based chimeric antigen receptor and application thereof. The chimeric antigen receptor prepared in the present application enhances the immune effect of T cells upon CAR stimulation signal and enhances the therapeutic effect of the CAR-T cells by genetically modifying the T cell signal.

To achieve this purpose, the present application adopts the following technical solutions:

In one aspect, the present application provides a CD19-based chimeric antigen receptor comprising an antigen-binding domain, a transmembrane domain, a costimulatory signal transduction region, a CD3ζ signal transduction domain, and an inducible suicide fusion domain in tandem arrangement;

wherein the antigen-binding domain binds to a tumor surface antigen, the antigen-binding domain is a single chain antibody against the tumor surface antigen CD19, the costimulatory signal transduction region comprises a CD27 signal transduction domain, and the inducible suicide fusion domain is iCasp9.

In the present application, through the binding of the antigen-binding domain to the tumor surface antigen CD19, and then the specific genetic modification to the intracellular signal of the T cell receptor, i.e. the CD27 signal transduction domain, the tumor surface antigen is allowed to specifically bind to the chimeric antigen receptor of the present application to transmit a more efficient T cell stimulation signal, and has a better effect than other chimeric antigen receptors and other tumor antigens, and the target is highly expressed, which also enhance the immune effect of the CAR-T cells.

Moreover, the inventors have found that through the binding of the T cell signal, i.e. the CD27 signal transduction domain to the inducible suicide fusion domain, and through optimizing and reforming, the chimeric antigen receptor of the present application has a better killing effect and is not easy to cause an immune factor storm, and is accompanied with a safe removal mechanism. These modifications allow a more effective, wide and safe application of the chimeric antigen receptor CD19 cells.

According to the present application, the genetically modified T cell chimeric receptor (CAR) and the single chain antibody (scFv) against the CD19 antigen-binding domain are exemplified below.

In the present application, the T cell receptor signal gene is specifically modified, so that the signal of the T cell receptor expressed by the modified sequence is more sustainable and slowly releases immune factors, which improves the safety of reactions in vivo.

According to the present application, the single-chain antibody against the tumor surface antigen CD19 has an amino acid sequence as shown in SEQ ID NO. 1 or an amino acid sequence having more than 90% homology thereto. The amino acid sequence as shown in SEQ ID NO. 1 is as follows:

DIQMTQTTSSLSASLGDRVTISCRASQDISKYLNWYQQKPDGTVK

LLIYHTSRLHSGVPSRFSGSGSGTDYSLTISNLEQEDIATYFCQQGN

TLPYTFGGGTKLEITGSTSGSGKPGSGEGSTKGEVKLQESGPGLVA

PSQSLSVTCTVSGVSLPDYGVSWIRQPPRKGLEWLGVIWGSETTY

YNSALKSRLTIIKDNSKSQVFLKMNSLQTDDTAIYYCAKHYYYGG

SYAMDYWGQGTSVTVSS.

According to the present application, the amino acid sequence having more than 90% homology can be replaced by other single chain antibodies or humanized CD19 single chain antibodies. The amino acid mutant having more than 90% homology still functions as a CD19 single-chain antibody.

According to the present application, the CD27 signal transduction domain has an amino acid sequence as shown in SEQ ID NO. 2, which is as follows: QRRKYRSNKGESPVEPAEPCHYSCPREEEGSTIP-IQEDYRKPEPACS P.

According to the present application, the inducible suicide fusion domain iCasp9 has an amino acid sequence as shown in SEQ ID NO. 3, which is as follows:

GSGATNFSLLKQAGDVEENPGPMGVQVETISPGDGRTFPKRGQTC

VVHYTGMLEDGKKVDSSRDRNKPFKFMLGKQEVIRGWEEGVAQ

MSVGQRAKLTISPDYAYGATGHPGIIPPHATLVFDVELLKLEGGGG

SGGGGSGAMVGALESLRGNADLAYILSMEPCGHCLIINNVNFCRE

SGLRTRTGSNIDCEKLRRRFSSLHFMVEVKGDLTAKKMVLALLEL

ARQDHGALDCCVVVILSHGCQASHLQFPGAVYGTDGCPVSVEKI

VNIFNGTSCPSLGGKPKLFFIQACGGEQKDHGFEVASTSPEDESPG

SNPEPDATPFQEGLRTFDQLDAISSLPTPSDIFVSYSTFPGFVSWRD

PKSGSWYVETLDDIFEQWAHSEDLQSLLLRVANAVSVKGIYKQMP

GCFNFLRKKLFFKTSAS.

According to the present application, the inducible suicide fusion domain is connected in tandem with the CD3ζ signal transduction domain via a 2A sequence. The 2A sequence will cause the protein expressed by the inducible suicide fusion domain to cleave off from the chimeric antigen receptor protein, thereby allowing the chimeric antigen receptor to exert its function. While the suicide fusion domain can be activated by injecting an activator, thereby causing the T cells expressing the chimeric antigen receptor to die to lose their functions.

According to the present application, the transmembrane domain is a CD28 transmembrane domain and/or a CD8α transmembrane domain. In some particular embodiments, the transmembrane domain can be selected or modified by amino acid substitution.

According to the present application, the costimulatory signal transduction region further comprises a CD28 signal transduction domain. A person skilled in the art can adjust the arrangement of the CD28 signal transduction domain and the CD27 signal transduction domain according to requirements. Different arrangements of the CD28 signal transduction domain and the CD27 signal transduction domain will not affect the chimeric antigen receptor. The present application employs a genetically modified sequence combination of CD28-CD27.

The CD28 extracellular signal transduction domain has an amino acid sequence as shown in SEQ ID NO. 6, which is as follows:

IEVMYPPPYLDNEKSNGTIIHVKGKHLCPSPLFPGPSKP;

The CD28 transmembrane region conduction domain has an amino acid sequence as shown in SEQ ID NO. 7, which is as follows: FWVLVVVGGVLACYSLLVTVAFIIFWV;

The CD28 intracellular signal transduction domain has an amino acid sequence as shown in SEQ ID NO. 8, which is as follows:

RSKRSRLLHSDYMNMTPRRPGPTRKHYQPYAPPRDFAAYRSAS.

According to the present application, the chimeric antigen receptor further comprises a signal peptide, which is a signal peptide capable of directing the transmembrane transfer of the chimeric antigen receptor. A person skilled in the art can select a signal peptide conventional in the art according to requirements. The signal peptide is a Secretory signal peptide, which has an amino acid sequence as shown in SEQ ID NO. 9, which is as follows: MLLLVTSLLLCELPHPAFL-LIP.

Further, the Secretory signal peptide is a signal peptide for the CD8a gene, and the Secretory signal peptide has an amino acid sequence as shown in SEQ ID NO. 10, which is as follows: MALPVTALLLPLALLLHAARP.

Alternatively, the Secretory signal peptide is a signal peptide for the GMCSFR gene, and the Secretory signal peptide has an amino acid sequence as shown in SEQ ID NO. 11, which is as follows:

MLLLVTSLLLCELPHPAFLLIP.

The chimeric antigen receptor of the present application may further comprise a hinge region, which can be selected by a person skilled in the art according to the actual situation, and which is not particularly limited herein. The presence of a hinge region will not affect the performance of the chimeric antigen receptor of the present application.

According to the present application, the chimeric antigen receptor comprises a signal peptide, an antigen-binding domain, a transmembrane domain, a costimulatory signal transduction domain, a CD3ζ signal transduction domain, a 2A sequence, and an inducible suicide fusion domain in tandem arrangement.

As a preferable technical solution, the chimeric antigen receptor is a Secretory signal peptide, a CD19 antigen-binding domain, a CD8α and/or CD28 transmembrane domain, a CD28 extracellular signal transduction domain, a CD28 intracellular signal transduction domain, a CD27 intracellular signal transduction domain, a CD3ζ intracellular signal transduction domain, a 2A sequence and a iCasp9 domain in tandem arrangement, which has a particular arrangement as follows: Secretory-CD19-CD28-CD27-CD3ζ-2A-iCasp9.

According to the present application, the chimeric antigen receptor Secretory-CD19-CD28-CD27-CD3ζ-2A-iCasp9 (4S-CAR19) has an amino acid sequence as shown in SEQ ID NO. 4 or an amino acid sequence having more than 80% homology thereto. The amino acid sequence as shown in SEQ ID NO. 4 is as follows:

MLLLVTSLLLCELPHPAFLLIPDIQMTQTTSSLSASLGDRVTISCRAS
QDISKYLNWYQQKPDGTVKLLIYHTSRLHSGVPSRFSGSGSGTDY
SLTISNLEQEDIATYFCQQGNTLPYTFGGGTKLEITGSTSGSGKPGS
GEGSTKGEVKLQESGPGLVAPSQSLSVTCTVSGVSLPDYGVSWIR
QPPRKGLEWLGVIWGSETTYYNSALKSRLTIIKDNSKSQVFLKMN
SLQTDDTAIYYCAKHYYYGGSYAMDYWGQGTSVTVSSAAAIEV
MYPPPYLDNEKSNGTIIHVKGKHLCPSPLFPGPSKPFWVLVVVGG
VLACYSLLVTVAFIIFWVRSKRSRLLHSDYMNMTPRRPGPTRKHY
QPYAPPRDFAAYRSASGGGGSGGGGSQRRKYRSNKGESPVEPAEP
CHYSCPREEEGSTIPIQEDYRKPEPACSPGGGGSGGGGSRVKFSRS
ADAPAYQQGQNQLYNELNLGRREEYDVLDKRRGRDPEMGGKPR
RKNPQEGLYNELQKDKMAEAYSEIGMKGERRRGKGHDGLYQGL
STATKDTYDALHMQALPPRTSGSGATNFSLLKQAGDVEENPGPM
GVQVETISPGDGRTFPKRGQTCVVHYTGMLEDGKKVDSSRDRNK
PFKFMLGKQEVIRGWEEGVAQMSVGQRAKLTISPDYAYGATGHP
GIIPPHATLVFDVELLKLEGGGGSGGGGSGAMVGALESLRGNADL
AYILSMEPCGHCLIINNVNFCRESGLRTRTGSNIDCEKLRRRFSSLH
FMVEVKGDLTAKKMVLALLELARQDHGALDCCVVVILSHGCQA
SHLQFPGAVYGTDGCPVSVEKIVNIFNGTSCPSLGGKPKLFFIQAC
GGEQKDHGFEVASTSPEDESPGSNPEPDATPFQEGLRTFDQLDAISS
LPTPSDIFVSYSTFPGFVSWRDPKSGSWYVETLDDIFEQWAHSEDL
QSLLLRVANAVSVKGIYKQMPGCFNFLRKKLFFKTSAS;

or according to the present application, the chimeric antigen receptor Secretory-CD19-CD28-CD27-CD3ζ-2A-iCasp9 (4S-CAR19) has a nucleic acid sequence as shown in SEQ ID NO. 5 or a nucleic acid sequence having more than 80% homology thereto. The nucleic acid sequence as shown in SEQ ID NO. 5 is as follows:

ATGCTGCTGCTGGTCACAAGCCTGCTGCTGTGCGAGCTGCCCC
ACCCCGCCTTTCTGCTGATCCCCGACATCCAGATGACCCAGACC
ACCAGCAGCCTGAGCGCCAGCCTGGGCGACAGAGTGACCATC
AGCTGCCGGGCCAGCCAGGACATCAGCAAGTACCTGAACTGGT
ATCAGCAGAAACCCGACGGCACCGTGAAGCTGCTGATCTACCA
CACCAGCCGGCTGCACAGCGGCGTGCCCAGCAGATTTTCTGGC
AGCGGATCTGGCACCGACTACAGCCTGACCATCTCCAACCTGG
AACAGGAAGATATCGCTACCTACTTCTGTCAGCAGGGCAACAC
CCTGCCCTACACCTTCGGCGGAGGCACCAAGCTGGAAATCACC
GGCAGCACCAGCGGCTCCGGCAAGCCTGGATCTGGCGAGGGC

AGCACCAAGGGCGAAGTGAAGCTGCAGGAAAGCGGCCCTGGC
CTGGTCGCCCCTAGCCAGAGCCTGTCCGTGACCTGTACCGTGTC
CGGCGTGTCCCTGCCCGACTACGGCGTGTCCTGGATCAGACAG
CCCCCCAGAAAGGGCCTGGAATGGCTGGGCGTGATCTGGGCA
GCGAGACAACCTACTACAACAGCGCCCTGAAGTCCCGGCTGAC
CATCATCAAGGACAACAGCAAGAGCCAGGTGTTCCTGAAGATG
AACAGCCTGCAGACCGACGACACCGCCATCTACTACTGCGCCA
AGCACTACTACTACGGCGGCAGCTACGCCATGGACTACTGGGG
CCAGGGCACCAGCGTGACAGTCTCTTCTGCGGCCGCAATTGAA
GTTATGTATCCTCCTCCTTACCTAGACAATGAGAAGAGCAATGG
AACCATTATCCATGTGAAAGGGAAACACCTTTGTCCAAGTCCCC
TATTTCCCGGACCTTCTAAGCCCTTTTGGGTGCTGGTGGTGGTT
GGGGGAGTCCTGGCTTGCTATAGCTTGCTAGTAACAGTGGCCTT
TATTATTTTCTGGGTGAGGAGTAAGAGGAGCAGGCTCCTGCACA
GTGACTACATGAACATGACTCCCCGCCGCCTGGGCCCACCCG
CAAGCATTACCAGCCCTATGCCCCACCACGCGACTTCGCAGCCT
ATCGCTCCGCTAGCGGAGGTGGAGGTTCTGGAGGTGGTGGAAG
TCAAAGAAGGAAGTACCGCAGCAACAAAGGAGAATCTCCCGT
CGAGCCAGCCGAGCCCTGTCATTATTCATGCCCAAGGGAGGAG
GAGGGAAGTACAATCCCAATTCAAGAAGACTACAGGAAGCCCG
AACCTGCATGCAGTCCAGGTGGAGGCGGTTCTGGAGGCGGTGG
CTCCCGGGTGAAATTCTCACGGTCTGCAGACGCACCCGCTTACC
AGCAAGGCCAGAACCAACTCTATAACGAGCTCAATCTAGGACG
AAGAGAGGAGTACGATGTTTTGGACAAGAGACGTGGCCGGGA
CCCTGAGATGGGGGGAAAGCCGAGAAGGAAGAACCCTCAGGA
AGGCCTGTACAATGAACTGCAGAAAGATAAGATGGCGGAGGCC
TACAGTGAGATTGGGATGAAAGGCGAGCGCCGGAGGGGCAAG
GGGCACGATGGCCTTTACCAGGGTCTCAGTACAGCCACCAAGG
ACACCTACGACGCCCTTCACATGCAGGCCCTGCCCCCTCGCACT
AGTGGCTCCGGAGCCACGAACTTCTCTCTGTTAAAGCAAGCAG
GAGACGTGGAAGAAAACCCCGGTCCCATGGGAGTGCAGGTGG
AAACCATCTCCCCAGGAGACGGGCGCACCTTCCCCAAGCGCGG
CCAGACCTGCGTGGTGCACTACACCGGGATGCTTGAAGATGGA
AAGAAAGTGGACTCCTCCCGGGACAGAAACAAGCCCTTTAAGT
TTATGCTAGGCAAGCAGGAGGTGATCCGAGGCTGGGAAGAAGG
GGTTGCCCAGATGAGTGTGGGTCAGAGAGCCAAACTGACTATA
TCTCCAGATTATGCCTATGGTGCCACTGGGCACCCAGGCATCAT
CCCACCACATGCCACTCTCGTCTTCGATGTGGAGCTTCTAAAAC
TGGAAGGTGGAGGCGGTTCAGGCGGCGGCGGCAGCGGCGCCA
TGGTCGGTGCTCTTGAGAGTTTGAGGGGAAATGCAGATTTGGC

-continued

```
TTACATCCTGAGCATGGAGCCCTGTGGCCACTGCCTCATTATCA

ACAATGTGAACTTCTGCCGTGAGTCCGGGCTCCGCACCCGCAC

TGGCTCCAACATCGACTGTGAGAAGTTGCGGCGTCGCTTCTCCT

CGCTGCATTTCATGGTGGAGGTGAAGGGCGACCTGACTGCCAA

GAAAATGGTGCTGGCTTTGCTGGAGCTGGCGCGGCAGGACCAC

GGTGCTCTGGACTGCTGCGTGGTGGTCATTCTCTCTCACGGCTG

TCAGGCCAGCCACCTGCAGTTCCCAGGGGCTGTCTACGGCACA

GATGGATGCCCTGTGTCGGTCGAGAAGATTGTGAACATCTTCAA

TGGGACCAGCTGCCCCAGCCTGGGAGGGAAGCCCAAGCTCTTT

TTCATCCAGGCCTGTGGTGGGGAGCAGAAAGACCATGGGTTTG

AGGTGGCCTCCACTTCCCCTGAAGACGAGTCCCCTGGCAGTAA

CCCCGAGCCAGATGCCACCCCGTTCCAGGAAGGTTTGAGGACC

TTCGACCAGCTGGACGCCATATCTAGTTTGCCCACACCCAGTGA

CATCTTTGTGTCCTACTCTACTTTCCCAGGTTTTGTTTCCTGGAG

GGACCCCAAGAGTGGCTCCTGGTACGTTGAGACCCTGGACGAC

ATCTTTGAGCAGTGGGCTCACTCTGAAGACCTGCAGTCCCTCCT

GCTTAGGGTCGCTAATGCTGTTTCGGTGAAAGGGATTTATAAAC

AGATGCCTGGTTGCTTTAATTTCCTCCGGAAAAAACTTTTCTTTA

AAACATCAGCTAGT.
```

In the present application, the chimeric antigen receptor further comprises a promoter, which is EF1a or CMV, or any thereof or at least two thereof.

According to the present application, the chimeric antigen receptor is transfected into T cells for expression by nucleic acid sequence encoding the same.

According to the present application, the transfection is performed via any one of a viral vector, a eukaryotic expression plasmid or an mRNA sequence, or a combination of at least two thereof, and transfected into T cells, preferably transfected into T cells via a viral vector.

Further, the viral vector is any one of a lentiviral vector or a retroviral vector, or a combination of at least two thereof, preferably a lentiviral vector.

In a second aspect, the present application provides a recombinant lentivirus, which is obtained by co-transfection of mammalian cells with a viral vector comprising the chimeric antigen receptor of the first aspect and packaging helper plasmids pNHP and pHEF-VSVG.

In the present application, the recombinant lentivirus can efficiently immunize cells including T cells, and is capable of preparing targeting T cells.

According to the present application, the mammalian cell is any one of a 293 cell, a 293T cell or a TE671 cell, or a combination of at least two thereof.

In a third aspect, the present application provides a T cell comprising the chimeric antigen receptor as described in the first aspect and/or the recombinant lentivirus as described in the second aspect.

In the present application, the T cell has a good targeting effect and is capable of releasing low dose of immune factors, and has a property of low toxic reaction.

In a fourth aspect, the present application provides a composition comprising any one of the chimeric antigen receptor as described in the first aspect, the recombinant lentivirus as described in the second aspect or the T cell as described in the third aspect, or a combination of at least two thereof.

In a fifth aspect, the present application provides the use of the chimeric antigen receptor as described in the first aspect, the recombinant lentivirus as described in the second aspect or the composition as described in the third aspect, in preparing chimeric antigen receptor T cells and its application in tumor therapeutic drugs.

Further, the tumor is a blood-associated neoplastic disease and/or a solid tumor. The neoplastic disease is selected from, but not limited to leukemia.

Compared with the prior art, the present application has the following beneficial effects:

(1) Through specific modification of the T cell chimeric receptor gene and through optimization and modification of the T cell signal transduction region, the chimeric antigen receptor of the present application is allowed to have a better killing effect and is not easy to cause an immune factor storm, and is accompanied with a safe removal mechanism. These modifications allow a more effective, wide and safe application of the chimeric antigen receptor CD19 cells;

(2) The chimeric antigen receptor of the present application, which targets CD19 that is highly expressed in leukemia and lymphoma, can specifically recognize a tumor surface antigen. Moreover, the chimeric antigen receptor causes a mild and effective response after recognizing the tumor surface antigen CD19, thus it has a safer effect than other chimeric antigen receptors, so that the immune effect of the CAR-T cells is enhanced as well as the safety of the CAR-T cells.

DESCRIPTION OF THE DRAWINGS

FIG. 2 (b) are dot plots showing the results of the flow cytometry analysis of primary B-ALL cells stained with an CD19 antibody, in which samples are obtained from the bone marrow of 3 B-ALL patients;

DETAILED DESCRIPTION

In order to further illustrate the technical measures adopted by the present invention and the effects thereof, the technical solutions of the present invention are further described below with reference to the accompanying drawings and specific embodiments, and however, the present invention is not limited to the scope of the embodiments.

In the examples, techniques or conditions, which are not specifically indicated, are performed according to techniques or conditions described in the literature of the art, or according to product instructions. The reagents or instruments for use, which are not indicated with manufacturers, are conventional products that are commercially available from many sources.

Figure 1:
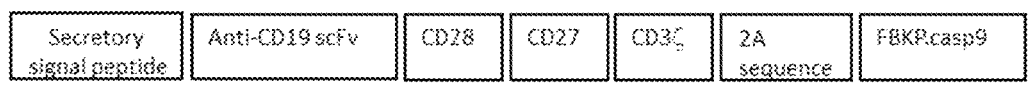
FIG. 1 shows a synthetic gene sequence map of the chimeric antigen receptor of the present application.

Example 1 Construction of Chimeric Antigen Receptors (1) The Secretory signal peptide, CD19 antigen-binding domain, CD8α and/or CD28 transmembrane domain, CD28 signal transduction domain, CD27 signal transduction domain, CD3ζ signal transduction domain, 2A sequence and Caspase 9 domain, as shown in FIG. 1, i.e. Secretory-CD19-CD28-CD27-CD3ζ-2A-iCasp9 was chemically synthesized by gene synthesis;

Example 2 Packaging of Lentivirus (1) 293T cells were used and cultured for 17-18 hours;
(2) Fresh DMEM containing 10% FBS was added;
(3) The following reagents were added to a sterile centrifuge tube: DMEM was taken for each well and helper DNA mix (pNHP, pHEF-VSV-G) and pTYF DNA vector were added, vortexed and shook;
(4) Superfect or any transgenic material was added to the centrifuge tube, left for 7-10 minutes at room temperature;
(5) To each culture cells the DNA-Superfect mixture in the centrifuge tube was added, vortexed and mixed;
(6) Cultured in a 3% $CO_2$ incubator at 37° C. for 4-5 hours;
(7) The supernatant was drawn from the culture medium, the culture was rinsed with 293 cell media, and media was added for further culture;
(8) The culture was returned to the 5% $CO_2$ incubator for overnight culture. The next morning and days later, transfection efficiency was observed with a fluorescence microscope if applicable.

Example 3 Purification and Concentration of Lentivirus

1) Purification of Virus
Cell debris were removed by a centrifugation at 1000 g for 5 minutes to obtain virus supernatant. The virus supernatant was filtered with a 0.45 µm low protein-binding filter, and the virus was divided into small portions and stored at −80° C.;
Typically, >$10^7$ transducing units of lentiviral vector can be produced by transfected cells per ml of medium.
2) Concentration of Lentivirus with a Centricon Filter
(1) The virus supernatant was added to the Centricon filter tube, then centrifuged at 2500 g for 30 minutes;
(2) The filter tube was shaken, then centrifuged at 400 g for 2 minutes, and the concentrated virus was collected to a collection cup. Finally, the virus was collected from all tubes into a single centrifuge tube.

Example 4 Transduction of CAR-T Cells

The activated T cells were seeded into a culture dish, and the concentrated lentivirus with specificity to target antigens was added, centrifuged at a rate of 100 g of centrifugal force for 100 minutes (spinoculation), then cultured at 37° C. for 24 hours, and AIM-V media containing cell culture factors were added, after 2-3 days of culture, the cells were harvested and counted to give available CD19 CAR-T cells.

Figure 2:
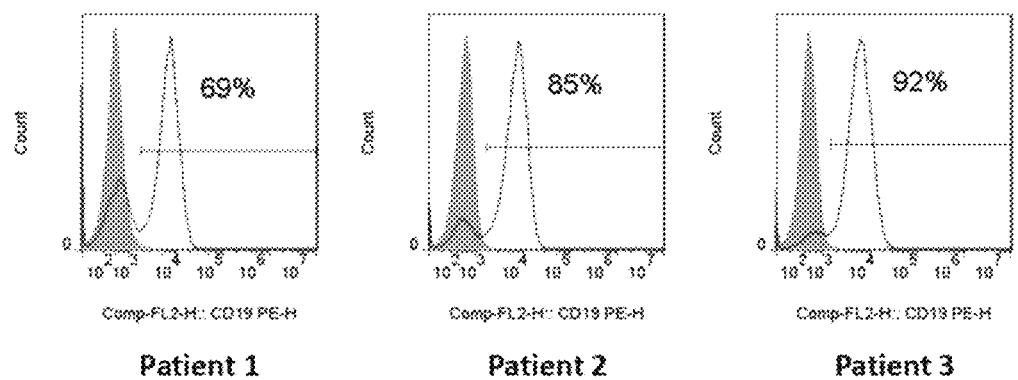
FIG. 2 (a) are histograms showing the results of the flow cytometry analysis of primary B-ALL cells using a CD19 antibody, in which samples are obtained from the bone marrow of 3 B-ALL (B cell acute lymphoblastic leukemia) patients and the gray area represents negative control of the same type.
Figure 2:
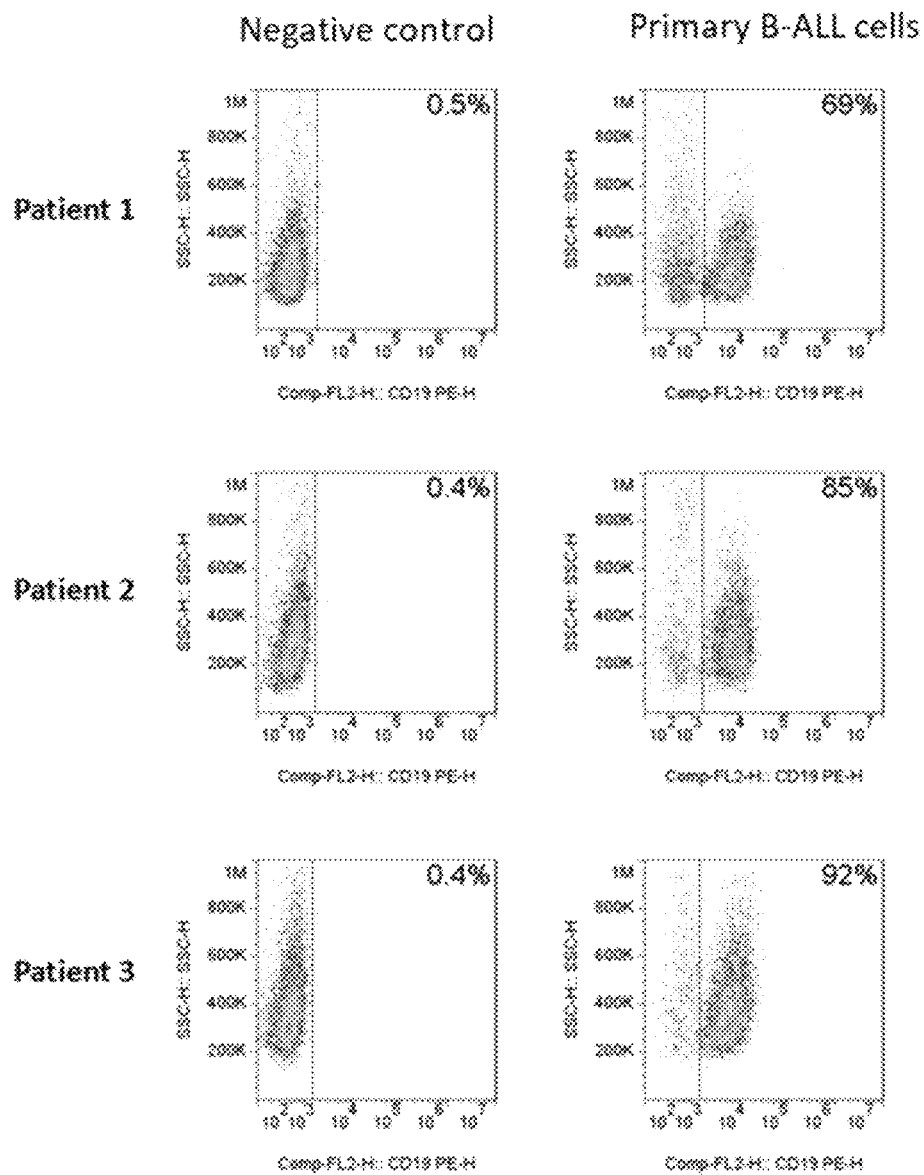

Example 5 Killing of Leukemia Cell Lines by CAR-T Cells In Vitro (1) It can be seen from FIGS. 2 (a) and 2 (b) that CD19 was highly expressed on the surface of primary bone marrow B-ALL cells and was widely expressed in patients with B-ALL, indicating that the CD19 chimeric antigen receptor selected for use in the present application can be used to treat B-ALL.
(2) In vitro evaluation of recognition and killing effects of CAR-T cells on target cells: non-specific T cells, GD2 CAR-T cells and specific 4S-CD19 CART (4S-CAR19) cells prepared in the present application were co-cultured with target cells expressing CD19 rather than GD2, i.e. RS4-11 (human acute lymphoblastic leukemia cell line) expressing GFP (T cells: RS4-11=3:1), in a 5% $CO_2$ incubator at 37° C. for 24 h;
(3) After the co-culture at different time points, cells were stained with Annexin V and PI and analyzed by flow cytometry. Wherein, AnnexinV positive cells were cells on the verge of apoptosis (early apoptosis) as a result of specific killing, AnnexinV and PI double positive cells were apoptotic cells as a result of specific killing, and PI positive cells were generally dead cells.

Figure 3:
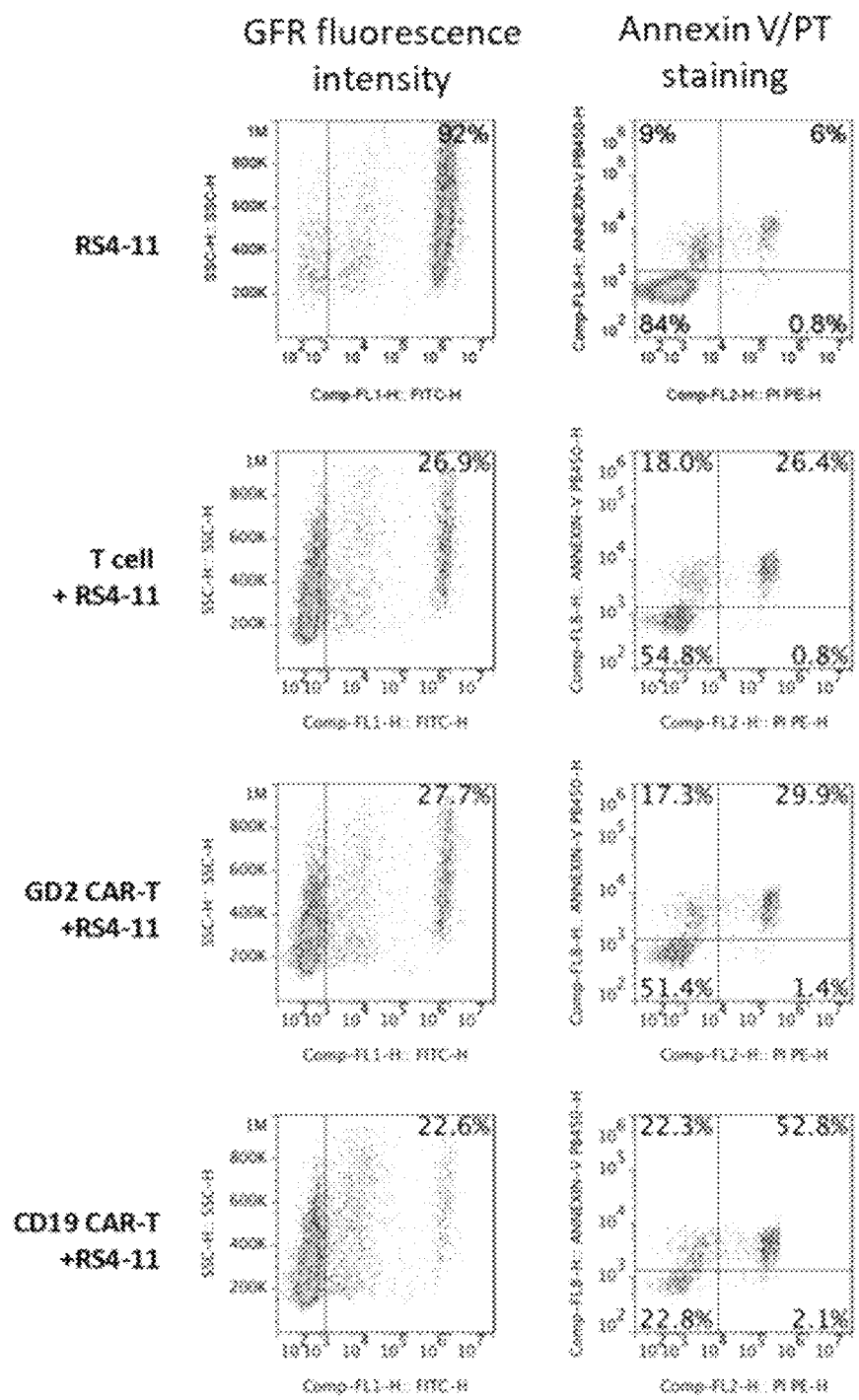
FIG. 3 shows the results of in vitro CD19-specific killing test of leukemia cell lines by CAR-T cells.

The results were shown in FIG. 3. It can be seen from the flow cytometry graph showing GFP fluorescence intensity that cells with a fluorescence intensity of $10^3$ or more were target RS4-11 tumor cells (GFP labeled), thus were gated for further analysis. When RS4-11 cells were co-cultured with no T cells, it was shown in the background that 9% of target cells were on the verge of apoptosis and 6% of target cells were apoptotic. When RS4-11 cells were co-cultured with unmodified general T cells, 18.0% of target cells were on the verge of apoptosis and 26.4% of target cells were apoptotic, which was taken as a non-specific killing background value. When RS4-11 cells were co-cultured with GD2 CAR-T cells, 17.3% of target cells were on the verge of apoptosis, and 29.9% of target cells were apoptotic, which was also taken as a non-specific killing background value. When RS4-11 cells were co-cultured with specific CD19 CAR-T cells, 22.3% of target cells were on the verge of apoptosis, and 52.8% of target cells were apoptotic, which was the effect of specific killing. It was shown that the numbers of target cells on the verge of apoptosis and of apoptotic target cells were significantly higher for T cells with a CD19 chimeric antigen receptor than other control groups, therefore the CD19 chimeric antigen receptor had an increased killing effect on target RS4-11 cells.

Figure 4:
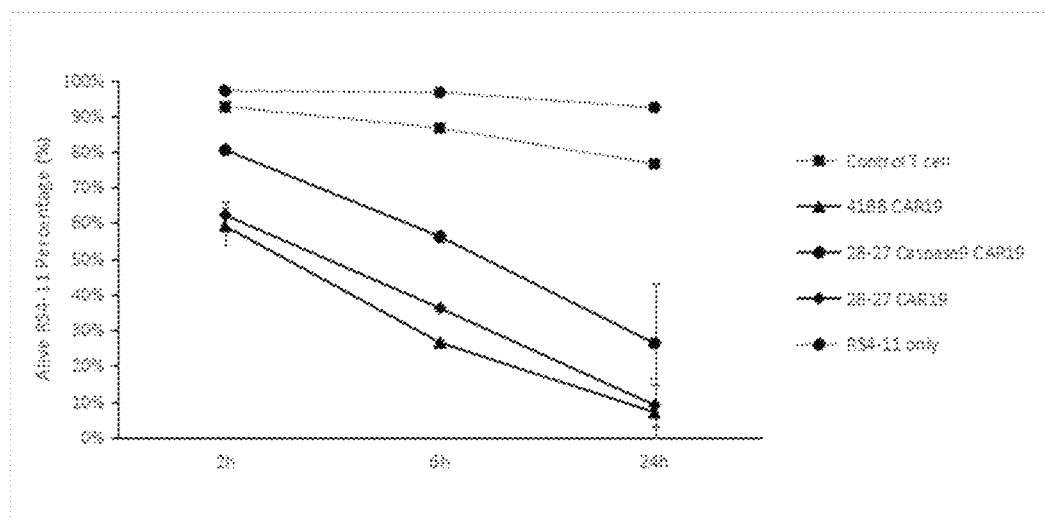
FIG. 4(a) shows a dynamic comparison of the in vitro killing ability between CD19 CAR-T cells with different signal transduction domains.
FIG. 4(b) shows a comparison of the ability between CD19 CAR-T cells with different signal transduction domains to release immune factors when killing in vitro.
Figure 4:
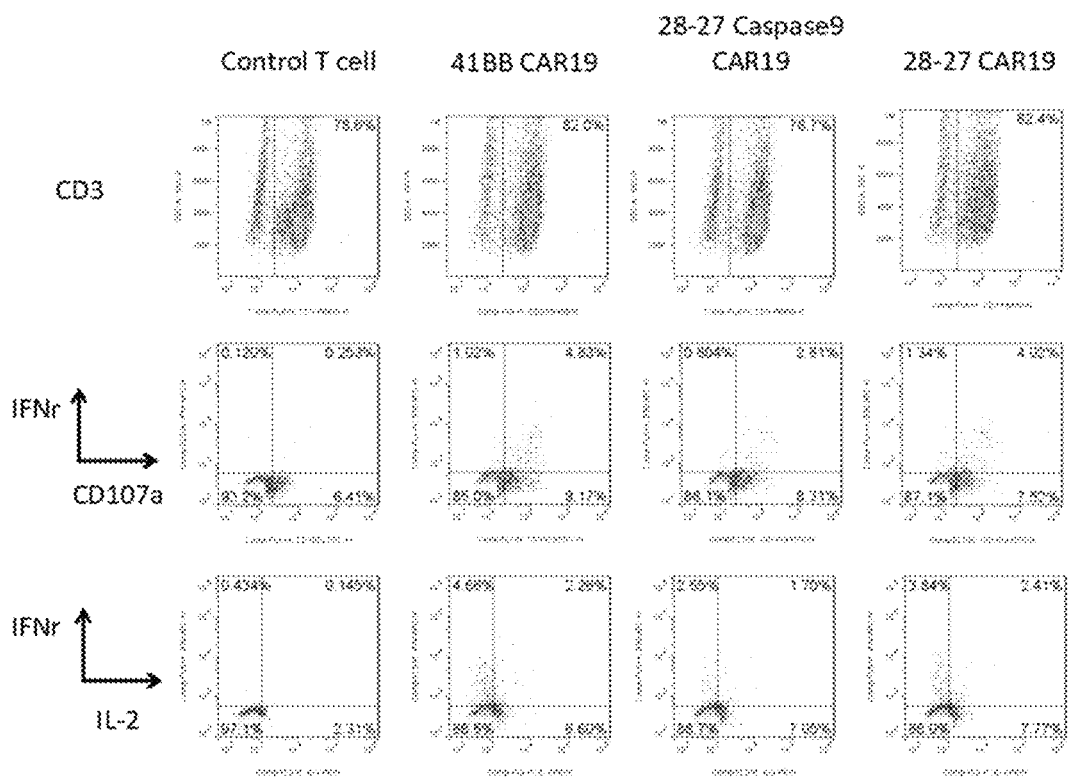

Example 6 Dynamic Comparison of In Vitro Killing by CD19 CAR-T Cells and Safety Test (1) Non-specific T cells or CD19 CAR-T cells comprising different signal transduction domains, including 41BB CAR19, 28-27 CAR19 and the 28-27 Caspase9 CAR19 (4S-CAR19) of the present application were co-cultured with RS4-11 in a 5% $CO_2$ incubator at 37° C. for 24 h. The percentage of alive RS4-11 cells was recorded at 2 hours, 6 hours, and 24 hours after the culture, and the results were shown in FIG. 4(a). The 41BB CAR19, 28-27 CAR19, and 28-27 Caspase9 CAR19 of the present application had significant killing effects on RS4-11 cells compared to T cells of the control group. As can be seen from the data obtained at 2 hours and 6 hours after the culture, the 28-27

Caspase9 CAR19 of the present application had a relatively slow killing dynamics, at 24 hours after the culture; however, a same killing effect as 41BB CAR19 and 28-27 CAR19 was achieved. It was shown that the leukemia cell ablation caused by the 28-27 Caspase9 CAR19 of the present application does not induce a severe toxicity response (cytokine release syndrome, CRS) in clinical application.

(2) Non-specific T cells or CD19 CAR-T cells comprising different signal transduction domains, including 41BB CAR19, 28-27 CAR19 and the 28-27 Caspase9 CAR19 of the present application were co-cultured with RS4-11 in a 5% $CO_2$ incubator at 37° C. After 6 h, the amount of immune factors produced by different CD19 CAR-T cells and degranulation effects were detected by an intracellular factor staining method, and the results were shown in FIG. 4(b). The 41BB CAR19, 28-27 CAR19, and the 28-27 Caspase9 CAR19 of the present application showed stronger (CD107a) degranulation ability and more interferon and interleukin-2 were produced compared to T cells of the control group. With regard to the percentage of cells producing interferon, it was 0.6% for T cells of the control group, 6.9% for the 41BB CAR19, 4.3% for the 28-27 Caspase9 CAR19, and 6.3% for the 28-27 CAR19. With regard to the percentage of cells producing interleukin-2, it was 2.5% for T cells of the control group, 8.9% for the 41BB CAR19, 8.8% for the 28-27 Caspase9 CAR19, and 10.2% for the 28-27 CAR19. It can be seen that after 6 hours of co-culture, the 28-27 Caspase9 CAR19 of the present application released lower amount of immune factors than CD19 CAR-T cells with other types of signal transduction domains. It can be inferred that the 28-27 Caspase9 CAR19 (4SCAR19) of the present application does not cause a severe immune factor storm (CRS) when used in clinical application, which enhances the safety of the therapy.

Example 7 Clinical Application of CAR-T Cells

The laboratory worked in cooperation with 22 clinical medical centers and hospitals from July 2013 to July 2016, and treated and closely followed 102 of CD19-positive and chemotherapy-tolerant B-ALL patients who met the enrollment criteria. There were a total of 55 children and 47 adults, 27 of which had undergone allogeneic hematopoietic stem cell transplantation. The patients had a median percentage of early leukemia cell blasts in bone marrow of 14.5% (ranging from 0% to 98%) at the time of receiving CAR-Ts. Among those patients, 69 patients had less than 50% of early leukemia blasts in bone marrow, and the other 33 patients had more than 50% of leukemia blasts in bone marrow. The median time period from initial diagnosis to CAR-T cell therapy was 17 months (range from 2 to 164 months).

Figure 5:
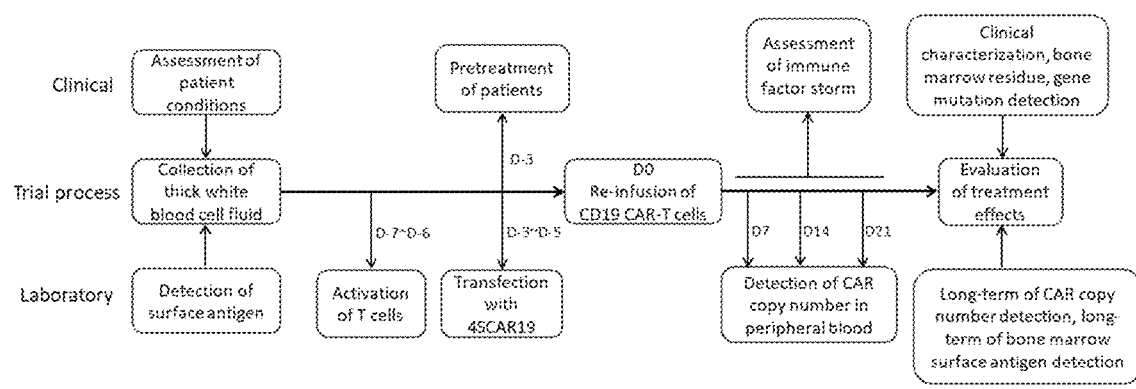
FIG. 5 shows a flow chart of clinical trial using CD19 CAR-T cells.

The flow chart of the clinical trial was shown in FIG. 5. The patients was first evaluated by the hospitals and the laboratory, and the autologous or donor white blood cells were collected if the enrollment conditions were met. Then following the standard protocol, CD3-positive T cells were screened from PBMC, activated and transfected with 4SCAR19 to prepare CD19 CAR-T cells. The patients were pretreated with cyclophosphamide and/or fludarabine prior to infusion. The average number of cells to be infused was $1.05 \times 10^6$ cells per kilogram of body weight. The quality of white blood cells and CAR-T cells, the gene transfection rate, the expansion of CAR-T cells and the effective number of infused CAR-T cells were evaluated and recorded. After the infusion of CAR-T cells into patients, the immune factor storm and CAR copy number were closely monitored within one month. The conclusion of treatment toxicity and final treatment outcomes are obtained by long-term of clinical and laboratory evaluations. Toxicity evaluation was performed based on the National Cancer Institute's Common Terminology Criteria for Adverse Events (CTCAE v4.03). The COX proportional hazard model was used to analyze the category variables and continuous variables, and the Kaplan-Meier curve was used for survival analysis. The results were shown in Tables 1-3.

Table 1 showed the remission rate and survival days of the patients.

|  | Total Patients | Children | Adults |
|---|---|---|---|
| Early Response |  |  |  |
| Complete Remission (CR) | 96 (87%) | 51 (88%) | 45 (87%) |
| No Remission (NR) | 14 (13%) | 7 (12%) | 7 (13%) |
| RFS, days |  |  |  |
| Median | 115.5 | 113.5 | 116.5 |
| Range | 0-455 | 0-450 | 0-455 |
| OS, days |  |  |  |
| Median | 222 | 250 | 207.5 |
| Range | 23-1041 | 30-1041 | 23-1003 |

There were a total of 110 patients who received CD19 CAR-T cell therapy in four years, from whom complete data were collected. Complete remission was achieved in 96 patients, including 51 children and 45 adults. The average number of days without recurrence exceeded 100 days, and the overall survival days exceeded 200 days. The results showed a good therapeutic effect of the 4SCAR19 T cells of the present application.

Table 2 showed the immune factor storm status of patients after the infusion of CAR-T cells.

|  |  | Total Patients | Malignant cells in bone marrow <50% | Malignant cells in bone marrow >=50% |
|---|---|---|---|---|
| Immune factor storm | Grade 0-2 | 97 (88%) | 67 (93%) | 30 (79%) |
|  | Grade 3-4 | 13 (12%) | 5 (7%) | 8 (21%) |

Among the patients with bone marrow malignant cells less than 50%, there were 55 patients who only had a Grade 0-1 immune factor storm response, and 17 patients had a Grade 2-4 response. Among patients with bone marrow malignant cells greater than or equal to 50%, there were 17 patients who had a Grade 0-1 grade immune factor storm response, and 21 patients had a Grade 2-4 grade response. Overall, 65% of patients only had a Grade 0-1 immune factor storm response, and there was no statistical correlation between the intensity of the response and the malignant cell load before the re-infusion. These results demonstrated the safety of the CD19 CAR-T cells of the present application.

Table 3 shows the expansion of CAR-T cells in vivo.

| CAR copy number in peripheral blood after the re-infusion | Total patients |
|---|---|
| 0% | 1 (1%) |
| >0%~1% | 60 (55%) |

-continued

| CAR copy number in peripheral blood after the re-infusion | Total patients |
|---|---|
| >1%~5% | 32 (29%) |
| >5% | 8 (7%) |

The number of CAR copies was detectable in peripheral blood within three weeks after the infusion of CAR-T cells into patients. Among the 101 patients whom have been collected data with, there was only one patient who had no detected copy number, and there were another 60 patients who had a detected copy number below 1%, 32 patients had a copy number from 1% to 5%, and still 8 patients had a detected copy number more than 5%. Due to the large number of peripheral blood cell bases, the detection of 1% of CAR copy number represented a significant amplification of CAR-T cells. It can be known from this table that the CD19 CAR-T cells of the present application were well expanded in vivo, and can well perform the function to kill cancer cells.

Figure 6:
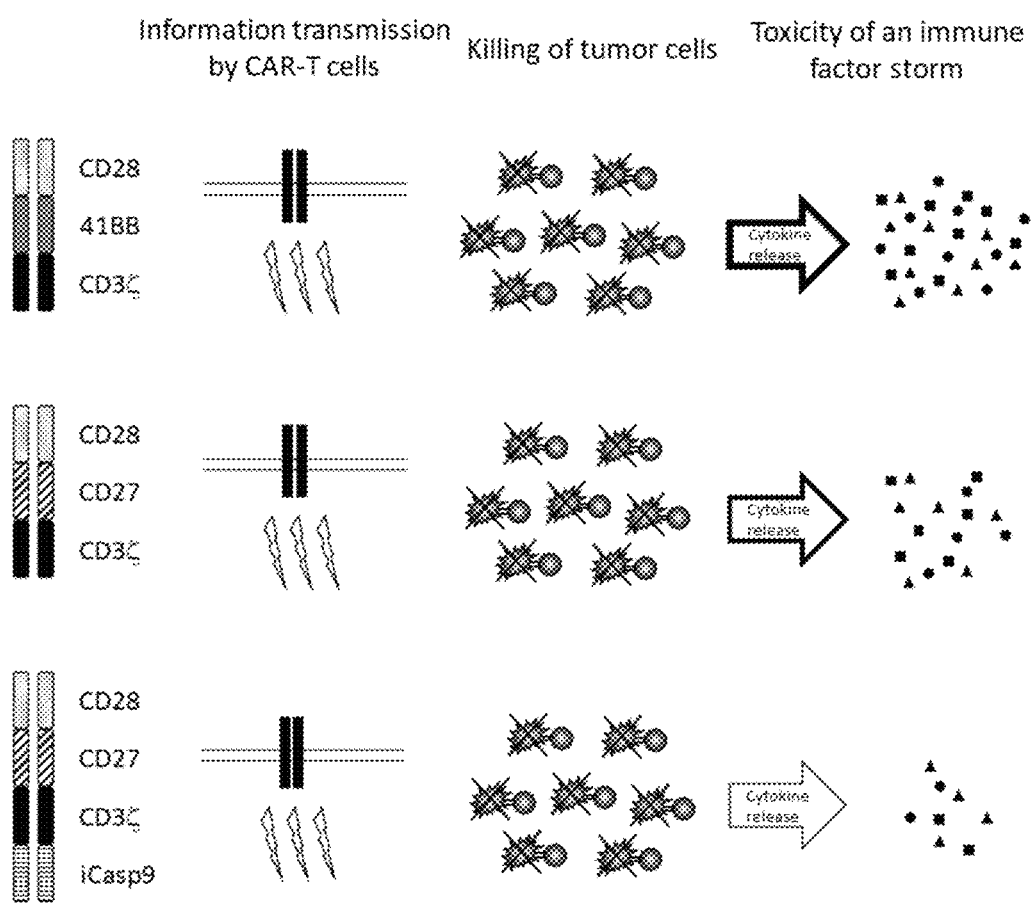
FIG. 6 shows a comparison between the effects of the chimeric antigen receptor of the present application and of other chimeric antigens.

In summary, the single-chain antibody of the chimeric antigen receptor of the present application against the CD19 tumor surface antigen is not prone to mutation escape. It can be seen from FIG. 6 that the chimeric antigen receptor of the present application had a better effect than other chimeric antigen receptors. Through optimization and modification of the T cell signal transduction region, the chimeric antigen receptor of the present application is allowed to have a better killing effect and does not induce a severe immune factor storm (CRS), and is accompanied with a safety designed removal mechanism, so that the immune effect of the CAR-T cells is enhanced, with increased therapeutic and safety effect of the CAR T cells.

The Applicant declares that detailed methods of the present application have been described through the above examples, and however, the present application is not limited to the above detailed methods. That is to say, it does not mean that the implementation of the present application must rely on the above detailed methods. Those skilled in the art should understand that any improvement on the present application, including the equivalent replacement of the raw materials or the addition of auxiliary components to the product of the present application, and the selection of specific methods, etc., falls within the protection scope and the disclosure scope of the present application.

What is claimed is:

1. A recombinant lentivirus encoding a chimeric antigen receptor binding CD19, wherein the recombinant lentivirus is obtained by co-transfection of a mammalian cell with a viral vector comprising the nucleic acid sequence of SEQ ID NO: 5 encoding the chimeric antigen receptor and packaging helper plasmids.

2. The recombinant lentivirus according to claim 1, wherein the chimeric antigen receptor comprises the amino acid sequence of SEQ ID NO: 4.

3. The recombinant lentivirus according to claim 1, wherein the recombinant lentivirus is transduced into T cells for expression.

4. The recombinant lentivirus according to claim 1, wherein the mammalian cell is any one of a 293 cell, a 293T cell or a TE671 cell.

5. A T cell transduced with the recombinant lentivirus according to claim 1.

6. A method of a tumor immunotherapy, comprising administrating a therapeutically effective amount of the T cell according to claim 5 to a patient in need thereof, wherein the tumor expresses CD19.

7. The method according to claim 6, wherein the tumor is a blood-associated neoplastic disease.

8. The method according to claim 7, wherein the blood-associated neoplastic disease is selected from leukemia or lymphoma.

9. A composition comprising the recombinant lentivirus according to claim 1.

* * * * *